(12) United States Patent
Zhou et al.

(10) Patent No.: US 8,377,035 B2
(45) Date of Patent: Feb. 19, 2013

(54) UNBALANCED REINFORCEMENT MEMBERS FOR MEDICAL DEVICE

(75) Inventors: Pu Zhou, Plymouth, MN (US); Ling Wang, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3341 days.

(21) Appl. No.: 10/346,697

(22) Filed: Jan. 17, 2003

(65) Prior Publication Data
US 2004/0143239 A1    Jul. 22, 2004

(51) Int. Cl.
*A61M 25/00* (2006.01)
(52) U.S. Cl. .................................................. 604/524
(58) Field of Classification Search .................. 604/19, 604/45, 93.01, 264, 523, 524, 526, 527, 528
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,437,542 A | 3/1948 | Krippendorf |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,416,531 A | 12/1968 | Edwards |
| 3,452,227 A | 6/1969 | Welch |
| 3,452,742 A | 7/1969 | Muller |
| 3,463,197 A * | 8/1969 | Slade .......................... 138/125 |

(Continued)

FOREIGN PATENT DOCUMENTS

| | | |
|---|---|---|
| AU | 723040 | 12/1997 |
| AU | 733966 | 4/1998 |

(Continued)

OTHER PUBLICATIONS

Webster's II New Riverside University Dictionary, ISBN 0-395-33957-X, 1994, p. 67.

*Primary Examiner* — Nicholas Lucchesi
*Assistant Examiner* — Jason Flick
(74) *Attorney, Agent, or Firm* — Seager, Tufte & Wickhem, LLC (57) ABSTRACT

A medical device shaft including an unbalanced braid reinforcement layer. The reinforcement layer may be an unbalanced braid by having a first set of strands and a second set of strands, the sets wound in opposing directions on a mandrel or on the device shaft. The first set and second set may have different numbers of strands, sizes of strands, or pitch, or combinations thereof. In some embodiments, the unbalanced braid increases contact area between the inner layer and the outer layer of the shaft without compromising the function of the braid. In other embodiments, the variations in strand size and number between the first set and the second set allows improved kink and torque performance in a reduced thickness braid layer. The improved shaft of the present invention may be incorporated into a wide variety of medical devices such as guide catheters, diagnostic catheters, balloon catheters, etc.

23 Claims, 3 Drawing Sheets

U.S. PATENT DOCUMENTS

| | | | |
|---|---|---|---|
| 3,463,953 A | 8/1969 | Maxwell | |
| 3,481,368 A | 12/1969 | Vansickle et al. | |
| 3,512,019 A | 5/1970 | Durand | |
| 3,544,868 A | 12/1970 | Bates | |
| 3,625,200 A | 12/1971 | Muller | |
| 3,686,990 A | 8/1972 | Margolien | |
| 3,731,671 A | 5/1973 | Mageoh | |
| 3,739,770 A | 6/1973 | Mori | |
| 3,841,308 A | 10/1974 | Tate | |
| 3,890,977 A | 6/1975 | Wilson | |
| 3,906,938 A | 9/1975 | Fleischhacker | |
| 3,924,632 A * | 12/1975 | Cook | 604/527 |
| 4,000,672 A | 1/1977 | Sitterer et al. | |
| 4,003,369 A | 1/1977 | Heilman et al. | |
| 4,020,829 A | 5/1977 | Willson et al. | |
| 4,030,503 A | 6/1977 | Clark, III | |
| 4,142,119 A | 2/1979 | Madey | |
| 4,215,703 A | 8/1980 | Wilson | |
| 4,279,252 A | 7/1981 | Martin | |
| 4,330,725 A | 5/1982 | Hintz | |
| 4,425,919 A | 1/1984 | Alston, Jr. et al. | |
| 4,430,083 A | 2/1984 | Ganz et al. | |
| 4,447,239 A | 5/1984 | Krutten | |
| 4,476,754 A | 10/1984 | Ducret | |
| 4,482,828 A | 11/1984 | Vergues et al. | |
| 4,484,586 A | 11/1984 | McMickle et al. | |
| 4,495,134 A | 1/1985 | Ouchi et al. | |
| 4,516,972 A | 5/1985 | Samson | |
| 4,545,390 A | 10/1985 | Leary | |
| 4,551,292 A | 11/1985 | Fletcher et al. | |
| 4,563,181 A | 1/1986 | Wijayarathna et al. | |
| 4,571,240 A | 2/1986 | Samson et al. | |
| 4,574,670 A | 3/1986 | Johnson | |
| 4,577,543 A * | 3/1986 | Wilson | 87/11 |
| 4,580,551 A | 4/1986 | Siegmund et al. | |
| 4,583,404 A | 4/1986 | Bernard et al. | |
| 4,635,270 A | 1/1987 | Gürs | |
| 4,636,346 A | 1/1987 | Gold et al. | |
| 4,657,024 A | 4/1987 | Coneys | |
| 4,665,906 A | 5/1987 | Jervis | |
| 4,676,249 A | 6/1987 | Arenas et al. | |
| 4,690,175 A | 9/1987 | Ouchi et al. | |
| 4,706,671 A | 11/1987 | Weinrib | |
| 4,719,924 A | 1/1988 | Crittenden et al. | |
| 4,721,117 A | 1/1988 | Mar et al. | |
| 4,737,153 A | 4/1988 | Shimamura et al. | |
| 4,762,130 A | 8/1988 | Fogarty et al. | |
| 4,763,647 A | 8/1988 | Gambale | |
| 4,764,324 A | 8/1988 | Burnham | |
| 4,774,949 A | 10/1988 | Fogarty | |
| 4,781,092 A | 11/1988 | Gaiser | |
| 4,781,186 A | 11/1988 | Simpson et al. | |
| 4,786,220 A | 11/1988 | Fildes et al. | |
| 4,790,331 A | 12/1988 | Okada et al. | |
| 4,800,890 A | 1/1989 | Cramer | |
| 4,811,743 A | 3/1989 | Stevens | |
| 4,813,434 A | 3/1989 | Buchbinder et al. | |
| 4,817,613 A | 4/1989 | Jaraczewski et al. | |
| 4,819,634 A | 4/1989 | Shiber | |
| 4,827,941 A | 5/1989 | Taylor et al. | |
| 4,830,023 A | 5/1989 | de Toledo et al. | |
| 4,831,858 A | 5/1989 | Yoshizawa | |
| 4,832,047 A | 5/1989 | Sepetka et al. | |
| 4,846,186 A | 7/1989 | Box et al. | |
| 4,846,193 A | 7/1989 | Tremulis et al. | |
| 4,863,442 A | 9/1989 | DeMello et al. | |
| 4,867,173 A | 9/1989 | Leoni | |
| 4,875,489 A | 10/1989 | Messner et al. | |
| 4,884,579 A | 12/1989 | Engelson | |
| 4,898,591 A | 2/1990 | Jang et al. | |
| 4,899,787 A | 2/1990 | Ouchi et al. | |
| 4,911,148 A | 3/1990 | Sosnowski et al. | |
| 4,917,102 A | 4/1990 | Miller et al. | |
| 4,922,164 A | 5/1990 | Jacobsen et al. | |
| 4,922,777 A | 5/1990 | Kawabata | |
| 4,932,419 A | 6/1990 | de Toledo | |
| 4,932,959 A | 6/1990 | Horzewski et al. | |
| 4,934,380 A | 6/1990 | Toledo | |
| 4,946,466 A | 8/1990 | Pinchuk et al. | |
| 4,953,553 A | 9/1990 | Tremulis | |
| 4,954,022 A | 9/1990 | Underwood et al. | |
| 4,955,384 A | 9/1990 | Taylor et al. | |
| 4,955,862 A | 9/1990 | Sepetka | |
| 4,960,410 A | 10/1990 | Pinchuk | |
| 4,964,409 A | 10/1990 | Tremulis | |
| 4,966,163 A | 10/1990 | Kraus et al. | |
| 4,968,306 A | 11/1990 | Huss et al. | |
| 4,979,951 A | 12/1990 | Simpson | |
| 4,981,478 A * | 1/1991 | Evard et al. | 604/527 |
| 4,985,022 A | 1/1991 | Fearnot et al. | |
| 4,989,608 A | 2/1991 | Ratner | |
| 4,990,143 A | 2/1991 | Sheridan | |
| 4,994,069 A | 2/1991 | Ritchart et al. | |
| 4,998,923 A | 3/1991 | Samson et al. | |
| 5,007,434 A | 4/1991 | Doyle et al. | |
| 5,009,137 A | 4/1991 | Dannatt | |
| 5,019,057 A * | 5/1991 | Truckai | 604/527 |
| 5,037,404 A * | 8/1991 | Gold et al. | 604/527 |
| 5,040,543 A | 8/1991 | Badera et al. | |
| 5,045,072 A | 9/1991 | Castillo et al. | |
| 5,050,606 A | 9/1991 | Tremulis | |
| 5,052,404 A | 10/1991 | Hodgson | |
| 5,057,092 A * | 10/1991 | Webster, Jr. | 604/527 |
| 5,059,177 A | 10/1991 | Alcebo et al. | |
| 5,063,935 A | 11/1991 | Gamble | |
| 5,065,769 A | 11/1991 | De Toledo | |
| 5,069,674 A | 12/1991 | Fearnot et al. | |
| 5,095,915 A | 3/1992 | Engelson | |
| 5,106,455 A | 4/1992 | Jacobsen et al. | |
| 5,109,830 A | 5/1992 | Cho | |
| 5,125,395 A | 6/1992 | Adair | |
| 5,135,531 A | 8/1992 | Shiber | |
| 5,144,959 A | 9/1992 | Gambale et al. | |
| 5,147,317 A | 9/1992 | Shank et al. | |
| 5,154,705 A | 10/1992 | Fleischhacker et al. | |
| 5,176,660 A * | 1/1993 | Truckai | 604/527 |
| 5,176,661 A * | 1/1993 | Evard et al. | 604/526 |
| 5,178,158 A | 1/1993 | de Toledo | |
| 5,180,376 A | 1/1993 | Fischell | |
| 5,181,668 A | 1/1993 | Tsuji et al. | |
| 5,184,627 A | 2/1993 | de Toledo | |
| 5,205,830 A | 4/1993 | Dassa et al. | |
| 5,211,183 A | 5/1993 | Wilson | |
| 5,217,440 A * | 6/1993 | Frassica | 604/524 |
| 5,217,482 A | 6/1993 | Keith | |
| 5,221,270 A | 6/1993 | Parker | |
| 5,228,441 A | 7/1993 | Lundquist | |
| 5,228,453 A | 7/1993 | Sepetka | |
| 5,238,004 A | 8/1993 | Sahatjian et al. | |
| 5,242,759 A | 9/1993 | Hall | |
| 5,243,996 A | 9/1993 | Hall | |
| 5,248,305 A | 9/1993 | Adrahala | |
| 5,250,069 A | 10/1993 | Nobuyoshi et al. | |
| 5,254,106 A | 10/1993 | Feaster | |
| 5,254,107 A | 10/1993 | Soltesz | |
| 5,256,144 A | 10/1993 | Kraus et al. | |
| 5,257,974 A | 11/1993 | Cox | |
| 5,259,393 A | 11/1993 | Corso, Jr. et al. | |
| 5,267,979 A | 12/1993 | Appling et al. | |
| 5,267,982 A | 12/1993 | Sylvanowicz | |
| 5,279,562 A | 1/1994 | Sirhan et al. | |
| 5,279,596 A | 1/1994 | Castaneda et al. | |
| 5,282,484 A | 2/1994 | Reger | |
| 5,284,128 A | 2/1994 | Hart | |
| 5,300,032 A | 4/1994 | Hibbs et al. | |
| 5,304,131 A | 4/1994 | Paskar | |
| 5,306,244 A | 4/1994 | Shiber | |
| 5,306,252 A | 4/1994 | Yutori et al. | |
| 5,308,435 A | 5/1994 | Ruggles et al. | |
| 5,313,967 A | 5/1994 | Lieber et al. | |
| 5,315,906 A | 5/1994 | Ferenczi et al. | |
| 5,315,996 A | 5/1994 | Lundquist | |
| 5,318,032 A | 6/1994 | Lonsbury et al. | |
| 5,318,529 A | 6/1994 | Kontos | |
| 5,322,064 A | 6/1994 | Lundquist | |
| 5,329,923 A | 7/1994 | Lundquist | |
| 5,333,620 A | 8/1994 | Moutafis et al. | |

| Patent No. | | Date | Inventor | Class |
|---|---|---|---|---|
| 5,334,145 A | | 8/1994 | Lundquist et al. | |
| 5,334,169 A | * | 8/1994 | Brown et al. | 604/527 |
| 5,336,205 A | | 8/1994 | Zenzen et al. | |
| 5,341,818 A | | 8/1994 | Abrams et al. | |
| 5,345,937 A | | 9/1994 | Middleman et al. | |
| 5,345,945 A | | 9/1994 | Hodgson et al. | |
| 5,353,808 A | | 10/1994 | Viera | |
| 5,354,623 A | | 10/1994 | Hall | |
| 5,358,493 A | | 10/1994 | Schweich et al. | |
| 5,358,796 A | | 10/1994 | Nakamura et al. | |
| 5,365,942 A | | 11/1994 | Shank | |
| 5,365,943 A | | 11/1994 | Jansen | |
| 5,368,564 A | | 11/1994 | Savage | |
| 5,368,661 A | | 11/1994 | Nakamura et al. | |
| 5,376,084 A | | 12/1994 | Bacich et al. | |
| 5,377,690 A | | 1/1995 | Berthiaume | |
| 5,381,782 A | | 1/1995 | DeLaRama et al. | |
| 5,403,292 A | | 4/1995 | Ju | |
| 5,406,960 A | | 4/1995 | Corso, Jr. | |
| 5,409,470 A | | 4/1995 | McIntyre et al. | |
| 5,411,476 A | | 5/1995 | Abrams | |
| 5,423,773 A | * | 6/1995 | Jimenez | 604/526 |
| 5,423,799 A | | 6/1995 | Shiu | |
| 5,437,288 A | | 8/1995 | Schwartz et al. | |
| 5,438,993 A | | 8/1995 | Lynch et al. | |
| 5,439,000 A | | 8/1995 | Gunderson et al. | |
| 5,441,483 A | | 8/1995 | Avitall | |
| 5,441,489 A | | 8/1995 | Utsumi et al. | |
| 5,447,812 A | | 9/1995 | Fukuda et al. | |
| 5,451,209 A | | 9/1995 | Ainsworth et al. | |
| 5,454,787 A | | 10/1995 | Lundquist | |
| 5,454,795 A | * | 10/1995 | Samson | 604/526 |
| 5,460,187 A | | 10/1995 | Daigle et al. | |
| 5,462,523 A | * | 10/1995 | Samson et al. | 604/30 |
| 5,465,710 A | * | 11/1995 | Miyagi et al. | 600/139 |
| 5,470,330 A | | 11/1995 | Goldenberg et al. | |
| 5,476,701 A | | 12/1995 | Berger | |
| 5,477,856 A | | 12/1995 | Lundquist | |
| 5,488,959 A | | 2/1996 | Ales | |
| 5,496,294 A | | 3/1996 | Hergenrother et al. | |
| 5,497,783 A | | 3/1996 | Urick et al. | |
| 5,497,785 A | | 3/1996 | Viera | |
| 5,499,973 A | | 3/1996 | Saab | |
| 5,507,301 A | | 4/1996 | Wasicek et al. | |
| 5,507,729 A | | 4/1996 | Lindenberg et al. | |
| 5,507,751 A | | 4/1996 | Goode et al. | |
| 5,507,766 A | | 4/1996 | Kugo et al. | |
| 5,514,128 A | | 5/1996 | Hillsman et al. | |
| 5,520,194 A | | 5/1996 | Miyata et al. | |
| 5,520,645 A | | 5/1996 | Imran et al. | |
| 5,531,719 A | | 7/1996 | Takahashi | |
| 5,533,985 A | | 7/1996 | Wang | |
| 5,533,987 A | | 7/1996 | Pray et al. | |
| 5,545,151 A | * | 8/1996 | O'Connor et al. | 604/524 |
| 5,546,958 A | | 8/1996 | Thorud et al. | |
| 5,551,443 A | | 9/1996 | Sepetka et al. | |
| 5,551,444 A | | 9/1996 | Finlayson | |
| 5,554,139 A | | 9/1996 | Okajima | |
| 5,562,619 A | | 10/1996 | Mirarchi et al. | |
| 5,569,197 A | | 10/1996 | Helmus et al. | |
| 5,569,200 A | | 10/1996 | Umeno et al. | |
| 5,569,218 A | | 10/1996 | Berg | |
| 5,569,220 A | * | 10/1996 | Webster, Jr. | 604/527 |
| 5,571,073 A | | 11/1996 | Castillo | |
| 5,573,520 A | | 11/1996 | Schwartz et al. | |
| 5,584,821 A | | 12/1996 | Hobbs et al. | |
| 5,591,142 A | * | 1/1997 | Van Erp | 604/526 |
| 5,599,326 A | | 2/1997 | Carter | |
| 5,599,492 A | | 2/1997 | Engelson | |
| 5,601,539 A | | 2/1997 | Corso, Jr. | |
| 5,603,705 A | | 2/1997 | Berg | |
| 5,605,162 A | | 2/1997 | Mirzaee et al. | |
| 5,622,184 A | | 4/1997 | Ashby et al. | |
| 5,630,806 A | | 5/1997 | Inagaki et al. | |
| 5,637,089 A | | 6/1997 | Abrams et al. | |
| 5,640,970 A | | 6/1997 | Arenas | |
| 5,656,011 A | | 8/1997 | Uihlein et al. | |
| 5,656,029 A | | 8/1997 | Imran et al. | |
| 5,658,263 A | | 8/1997 | Dang et al. | |
| 5,658,264 A | | 8/1997 | Samson et al. | |
| 5,662,622 A | | 9/1997 | Gore et al. | |
| 5,664,580 A | | 9/1997 | Erickson et al. | |
| 5,666,968 A | | 9/1997 | Imran et al. | |
| 5,666,969 A | | 9/1997 | Urick et al. | |
| 5,667,499 A | * | 9/1997 | Welch et al. | 604/528 |
| 5,669,926 A | | 9/1997 | Aust et al. | |
| 5,674,208 A | | 10/1997 | Berg et al. | |
| 5,676,659 A | | 10/1997 | McGurk | |
| 5,676,697 A | | 10/1997 | McDonald | |
| 5,682,894 A | | 11/1997 | Orr et al. | |
| 5,683,370 A | | 11/1997 | Luther et al. | |
| 5,690,120 A | | 11/1997 | Jacobsen et al. | |
| 5,695,506 A | | 12/1997 | Pike et al. | |
| 5,702,373 A | | 12/1997 | Samson | |
| 5,706,826 A | | 1/1998 | Schwager | |
| 5,720,300 A | | 2/1998 | Fagan et al. | |
| 5,722,609 A | | 3/1998 | Murakami | |
| 5,728,063 A | | 3/1998 | Preissman et al. | |
| 5,730,733 A | * | 3/1998 | Mortier et al. | 604/527 |
| 5,738,742 A | * | 4/1998 | Stevens | 156/149 |
| 5,741,429 A | | 4/1998 | Donadio, III et al. | |
| 5,746,696 A | | 5/1998 | Kondo | |
| 5,746,701 A | | 5/1998 | Noone | |
| 5,755,704 A | * | 5/1998 | Lunn | 604/527 |
| 5,769,830 A | | 6/1998 | Parker | |
| 5,772,609 A | | 6/1998 | Nguyen et al. | |
| 5,776,100 A | | 7/1998 | Forman | |
| 5,779,721 A | | 7/1998 | Nash | |
| 5,782,809 A | | 7/1998 | Umeno et al. | |
| 5,782,811 A | * | 7/1998 | Samson et al. | 604/527 |
| 5,788,653 A | | 8/1998 | Lorenzo | |
| 5,788,654 A | | 8/1998 | Schwager | |
| 5,788,707 A | | 8/1998 | Del Toro et al. | |
| 5,792,124 A | | 8/1998 | Horrigan et al. | |
| 5,795,341 A | | 8/1998 | Samson | |
| 5,797,856 A | | 8/1998 | Frisbie et al. | |
| 5,800,454 A | | 9/1998 | Jacobsen et al. | |
| 5,807,075 A | | 9/1998 | Jacobsen et al. | |
| 5,807,249 A | | 9/1998 | Qin et al. | |
| 5,810,885 A | | 9/1998 | Zinger | |
| 5,813,996 A | | 9/1998 | St. Germain et al. | |
| 5,820,612 A | | 10/1998 | Berg | |
| 5,827,225 A | | 10/1998 | Ma Schwab | |
| 5,827,242 A | | 10/1998 | Follmer et al. | |
| 5,833,632 A | | 11/1998 | Jacobsen et al. | |
| 5,836,926 A | | 11/1998 | Peterson et al. | |
| 5,843,050 A | | 12/1998 | Jones et al. | |
| 5,843,244 A | | 12/1998 | Pelton et al. | |
| 5,851,203 A | | 12/1998 | van Muiden | |
| 5,876,386 A | * | 3/1999 | Samson | 604/524 |
| 5,885,207 A | * | 3/1999 | Iwasaka | 600/139 |
| 5,891,112 A | * | 4/1999 | Samson | 604/524 |
| 5,891,114 A | * | 4/1999 | Chien et al. | 604/527 |
| 5,895,378 A | | 4/1999 | Nita | |
| 5,897,537 A | | 4/1999 | Berg et al. | |
| 5,899,892 A | | 5/1999 | Mortier et al. | |
| 5,902,254 A | | 5/1999 | Magram | |
| 5,902,290 A | | 5/1999 | Peacock, III et al. | |
| 5,904,657 A | | 5/1999 | Unsworth et al. | |
| 5,906,618 A | | 5/1999 | Larson, III | |
| 5,911,715 A | | 6/1999 | Berg et al. | |
| 5,911,717 A | | 6/1999 | Jacobsen et al. | |
| 5,927,345 A | * | 7/1999 | Samson | 138/127 |
| 5,931,830 A | | 8/1999 | Jacobsen et al. | |
| 5,935,108 A | | 8/1999 | Katoh et al. | |
| 5,938,653 A | * | 8/1999 | Pepin | 604/527 |
| 5,947,939 A | | 9/1999 | Mortier et al. | |
| 5,947,940 A | | 9/1999 | Beisel | |
| 5,951,496 A | | 9/1999 | Willi | |
| 5,951,539 A | | 9/1999 | Nita et al. | |
| 5,954,651 A | * | 9/1999 | Berg et al. | 600/434 |
| 5,957,910 A | * | 9/1999 | Holden et al. | 604/527 |
| 5,971,975 A | | 10/1999 | Mills et al. | |
| 5,972,019 A | | 10/1999 | Engelson et al. | |
| 5,980,471 A | | 11/1999 | Jafari | |
| 5,984,877 A | | 11/1999 | Fleischhacker, Jr. | |
| 6,001,068 A | | 12/1999 | Uchino et al. | |
| 6,004,279 A | | 12/1999 | Crowley et al. | |

| | | | | | | |
|---|---|---|---|---|---|---|
| 6,014,919 | A | 1/2000 | Jacobsen et al. | 6,440,088 | B1 | 8/2002 | Jacobsen |
| 6,017,319 | A | 1/2000 | Jacobsen et al. | 6,443,925 | B1 | 9/2002 | Schaible et al. |
| 6,017,335 | A * | 1/2000 | Burnham ............... 604/527 | 6,458,137 | B1 | 10/2002 | Klint |
| 6,019,772 | A | 2/2000 | Shefram et al. | 6,461,311 | B2 | 10/2002 | DuBois et al. |
| 6,022,343 | A | 2/2000 | Johnson et al. | 6,478,778 | B1 | 11/2002 | Jacobsen et al. |
| 6,022,369 | A | 2/2000 | Jacobsen et al. | 6,485,457 | B1 * | 11/2002 | Hisamatsu et al. ...... 604/102.02 |
| 6,024,730 | A | 2/2000 | Pagan | 6,488,637 | B1 | 12/2002 | Eder et al. |
| 6,027,461 | A | 2/2000 | Walker et al. | 6,491,648 | B1 | 12/2002 | Cornish et al. |
| 6,030,371 | A * | 2/2000 | Pursley ............... 604/527 | 6,491,671 | B1 | 12/2002 | Larson, III et al. |
| 6,042,553 | A | 3/2000 | Solar et al. | 6,494,894 | B2 | 12/2002 | Mirarchi |
| 6,042,578 | A * | 3/2000 | Dinh et al. ............ 604/527 | 6,503,244 | B2 | 1/2003 | Hayman |
| 6,045,547 | A | 4/2000 | Ren et al. | 6,508,803 | B1 | 1/2003 | Horikawa et al. |
| 6,048,339 | A | 4/2000 | Zirps et al. | 6,508,805 | B1 * | 1/2003 | Garabedian et al. ......... 604/524 |
| 6,053,904 | A | 4/2000 | Scribner et al. | 6,508,806 | B1 * | 1/2003 | Hoste ............... 604/524 |
| 6,056,702 | A | 5/2000 | Lorenzo | 6,511,462 | B1 * | 1/2003 | Itou et al. ............. 604/264 |
| 6,063,101 | A | 5/2000 | Jacobsen et al. | 6,524,301 | B1 | 2/2003 | Wilson et al. |
| 6,063,200 | A | 5/2000 | Jacobsen et al. | 6,527,732 | B1 | 3/2003 | Strauss et al. |
| 6,066,361 | A | 5/2000 | Jacobsen et al. | 6,530,934 | B1 | 3/2003 | Jacobsen et al. |
| 6,099,561 | A | 8/2000 | Alt | 6,544,197 | B2 | 4/2003 | DeMello |
| 6,102,890 | A | 8/2000 | Svitland et al. | 6,547,779 | B2 | 4/2003 | Levine et al. |
| 6,106,485 | A | 8/2000 | McMahon | 6,553,880 | B2 | 4/2003 | Jacobsen et al. |
| 6,106,488 | A | 8/2000 | Fleming et al. | 6,556,873 | B1 | 4/2003 | Smits |
| 6,112,771 | A * | 9/2000 | Aoyagi et al. ............. 138/127 | 6,562,022 | B2 * | 5/2003 | Hoste et al. ............. 604/524 |
| 6,139,510 | A | 10/2000 | Palermo | 6,579,246 | B2 | 6/2003 | Jacobsen et al. |
| 6,143,013 | A * | 11/2000 | Samson et al. ............. 606/192 | 6,591,472 | B1 * | 7/2003 | Noone et al. ............. 29/417 |
| 6,152,911 | A | 11/2000 | Giannoble | 6,602,207 | B1 | 8/2003 | Mam et al. |
| 6,152,912 | A * | 11/2000 | Jansen et al. ............. 604/526 | 6,602,280 | B2 | 8/2003 | Chobotov |
| 6,165,163 | A * | 12/2000 | Chien et al. ............. 604/523 | 6,610,046 | B1 | 8/2003 | Usami et al. |
| 6,165,292 | A | 12/2000 | Abrams et al. | 6,623,448 | B2 | 9/2003 | Slater |
| 6,171,295 | B1 * | 1/2001 | Garabedian et al. ......... 604/524 | 6,626,889 | B1 * | 9/2003 | Simpson et al. ............. 604/524 |
| 6,171,296 | B1 | 1/2001 | Chow | 6,636,758 | B2 | 10/2003 | Sanchez et al. |
| 6,183,410 | B1 | 2/2001 | Jacobsen et al. | 6,638,266 | B2 | 10/2003 | Wilson et al. |
| 6,193,686 | B1 | 2/2001 | Estrada et al. | 6,652,508 | B2 | 11/2003 | Griffin et al. |
| 6,197,014 | B1 * | 3/2001 | Samson et al. ............. 604/524 | 6,669,886 | B1 * | 12/2003 | Willard ............... 264/171.14 |
| 6,203,485 | B1 | 3/2001 | Urick | 6,682,493 | B2 | 1/2004 | Mirigian |
| RE37,148 | E | 4/2001 | Shank | 6,684,874 | B2 | 2/2004 | Mizek et al. |
| 6,213,995 | B1 * | 4/2001 | Steen et al. ............. 604/527 | 6,689,120 | B1 * | 2/2004 | Gerdts ............... 604/526 |
| 6,214,042 | B1 | 4/2001 | Jacobsen et al. | 6,702,762 | B2 | 3/2004 | Jafari et al. |
| 6,217,565 | B1 | 4/2001 | Cohen | 6,709,429 | B1 * | 3/2004 | Schaefer et al. ............. 604/527 |
| 6,228,073 | B1 | 5/2001 | Noone et al. | 6,712,826 | B2 | 3/2004 | Lui |
| 6,235,042 | B1 | 5/2001 | Katzman | 6,730,095 | B2 | 5/2004 | Olson, Jr. et al. |
| 6,245,053 | B1 * | 6/2001 | Benjamin ............... 604/523 | 6,740,073 | B1 * | 5/2004 | Saville ............... 604/524 |
| 6,245,068 | B1 | 6/2001 | Olson et al. | 6,749,560 | B1 | 6/2004 | Konstorum et al. |
| 6,248,082 | B1 | 6/2001 | Jafari | 6,766,720 | B1 | 7/2004 | Jacobsen et al. |
| 6,251,092 | B1 | 6/2001 | Qin et al. | 6,777,644 | B2 | 8/2004 | Peacock, III et al. |
| 6,254,549 | B1 | 7/2001 | Ramzipoor | 6,811,544 | B2 | 11/2004 | Schaer |
| 6,258,080 | B1 * | 7/2001 | Samson ............... 604/525 | 6,826,473 | B1 | 11/2004 | Burch et al. |
| 6,260,458 | B1 | 7/2001 | Jacobsen et al. | 6,837,898 | B2 | 1/2005 | Boyle et al. |
| 6,273,404 | B1 | 8/2001 | Holman et al. | 6,846,535 | B2 * | 1/2005 | De Groot et al. ............. 428/36.9 |
| 6,273,876 | B1 | 8/2001 | Klima et al. | 6,866,642 | B2 | 3/2005 | Kellerman et al. |
| 6,273,879 | B1 | 8/2001 | Keith et al. | 6,866,660 | B2 * | 3/2005 | Garabedian et al. ......... 604/527 |
| 6,290,656 | B1 | 9/2001 | Boyle et al. | 6,875,949 | B2 | 4/2005 | Hall |
| 6,290,692 | B1 | 9/2001 | Klima et al. | 6,887,235 | B2 | 5/2005 | O'Connor et al. |
| 6,296,616 | B1 | 10/2001 | McMahon | 6,918,882 | B2 | 7/2005 | Skujins et al. |
| 6,296,631 | B2 | 10/2001 | Chow | 6,942,654 | B1 * | 9/2005 | Schaefer et al. ............. 604/527 |
| 6,302,870 | B1 | 10/2001 | Jacobsen et al. | 6,997,937 | B2 | 2/2006 | Jacobsen et al. |
| 6,306,105 | B1 | 10/2001 | Rooney et al. | 7,001,369 | B2 | 2/2006 | Griffin et al. |
| 6,322,534 | B1 | 11/2001 | Shkolnik | 7,074,197 | B2 | 7/2006 | Reynolds et al. |
| 6,325,790 | B1 | 12/2001 | Trotta | 7,153,277 | B2 | 12/2006 | Skujins et al. |
| 6,338,725 | B1 | 1/2002 | Hermann et al. | 7,169,118 | B2 | 1/2007 | Reynolds et al. |
| 6,346,091 | B1 | 2/2002 | Jacobsen et al. | 7,182,735 | B2 | 2/2007 | Shireman et al. |
| 6,348,041 | B1 | 2/2002 | Klint | 2001/0014770 | A1 | 8/2001 | Olson et al. |
| 6,352,515 | B1 | 3/2002 | Anderson et al. | 2002/0019599 | A1 | 2/2002 | Rooney et al. |
| 6,355,005 | B1 | 3/2002 | Powell et al. | 2002/0045855 | A1 | 4/2002 | Frassica |
| 6,355,027 | B1 | 3/2002 | Le et al. | 2002/0072729 | A1 * | 6/2002 | Hoste et al. ............. 604/524 |
| 6,358,238 | B1 | 3/2002 | Sherry | 2003/0009184 | A1 | 1/2003 | Pepin |
| 6,358,256 | B1 | 3/2002 | Reinhardt | 2003/0009208 | A1 | 1/2003 | Snyder et al. |
| 6,368,315 | B1 | 4/2002 | Gillis et al. | 2003/0032897 | A1 | 2/2003 | Burmeister et al. |
| 6,368,316 | B1 * | 4/2002 | Jansen et al. ............. 604/526 | 2003/0060732 | A1 | 3/2003 | Jacobsen et al. |
| 6,375,628 | B1 | 4/2002 | Zadno-Azizi et al. | 2003/0069521 | A1 | 4/2003 | Reynolds et al. |
| 6,375,774 | B1 | 4/2002 | Lunn et al. | 2003/0069522 | A1 | 4/2003 | Jacobsen et al. |
| 6,379,369 | B1 | 4/2002 | Abrams et al. | 2003/0139763 | A1 | 7/2003 | Duerig et al. |
| 6,383,146 | B1 | 5/2002 | Klint | 2003/0216668 | A1 | 11/2003 | Howland et al. |
| 6,387,121 | B1 | 5/2002 | Alt | 2004/0010194 | A1 | 1/2004 | Kamiyama |
| 6,390,993 | B1 | 5/2002 | Cornish et al. | 2004/0116831 | A1 | 6/2004 | Vrba |
| 6,398,758 | B1 | 6/2002 | Jacobsen et al. | 2004/0122340 | A1 | 6/2004 | Vrba et al. |
| 6,428,489 | B1 | 8/2002 | Jacobsen et al. | 2004/0142643 | A1 | 7/2004 | Miller et al. |
| 6,428,512 | B1 | 8/2002 | Anderson et al. | 2004/0153049 | A1 * | 8/2004 | Hewitt et al. ............. 604/527 |
| 6,431,039 | B1 | 8/2002 | Jacobsen et al. | 2004/0167437 | A1 | 8/2004 | Sharrow et al. |

| | | | | | | |
|---|---|---|---|---|---|---|
| 2004/0167441 | A1 | 8/2004 | Reynolds et al. | JP | 4-213070 | 8/1992 |
| 2004/0167442 | A1 | 8/2004 | Shireman et al. | JP | 4-236965 | 8/1992 |
| 2004/0176740 | A1* | 9/2004 | Chouinard ............... 604/527 | JP | 5-149969 | 6/1993 |
| 2004/0181174 | A2 | 9/2004 | Davis et al. | JP | 5-506806 | 10/1993 |
| 2004/0181176 | A1 | 9/2004 | Jafari et al. | JP | 5-309519 | 11/1993 |
| 2004/0193140 | A1 | 9/2004 | Griffin et al. | JP | 5-507857 | 11/1993 |
| 2005/0054950 | A1 | 3/2005 | Parins | JP | 6-501179 | 2/1994 |
| 2006/0100687 | A1 | 5/2006 | Fahey et al. | JP | 6-169996 | 6/1994 |
| 2006/0121218 | A1 | 6/2006 | Obara et al. | JP | 6-312313 | 11/1994 |
| 2006/0122537 | A1 | 6/2006 | Reynolds et al. | JP | 7-124164 | 5/1995 |
| 2006/0189896 | A1 | 8/2006 | Davis et al. | JP | 7-124263 | 5/1995 |
| 2006/0264904 | A1 | 11/2006 | Kerby et al. | JP | 7-136280 | 5/1995 |
| 2007/0083132 | A1 | 4/2007 | Sharrow | JP | 7-148264 | 6/1995 |
| 2007/0255183 | A1 | 11/2007 | Chen | JP | 7-505561 | 6/1995 |
| 2008/0021347 | A1 | 1/2008 | Jacobsen et al. | JP | 7-37199 | 7/1995 |
| 2008/0021348 | A1 | 1/2008 | Jacobsen et al. | JP | 7-185009 | 7/1995 |
| 2008/0021400 | A1 | 1/2008 | Jacobsen et al. | JP | 7-255855 | 10/1995 |
| 2008/0021401 | A1 | 1/2008 | Jacobsen et al. | JP | 7-265319 | 10/1995 |
| 2008/0021402 | A1 | 1/2008 | Jacobsen et al. | JP | 7-275366 | 10/1995 |
| 2008/0021403 | A1 | 1/2008 | Jacobsen et al. | JP | 8-229888 | 9/1996 |
| 2008/0021404 | A1 | 1/2008 | Jacobsen et al. | JP | 8-509141 | 10/1996 |
| 2008/0021405 | A1 | 1/2008 | Jacobsen et al. | JP | 8-317986 | 12/1996 |
| 2008/0021406 | A1 | 1/2008 | Jacobsen et al. | JP | 8-317988 | 12/1996 |
| 2008/0021407 | A1 | 1/2008 | Jacobsen et al. | JP | 9-000164 | 4/1997 |
| 2008/0021408 | A1 | 1/2008 | Jacobsen et al. | JP | 9-276413 | 10/1997 |
| 2008/0064989 | A1 | 3/2008 | Chen et al. | JP | 9-294813 A | 11/1997 |
| 2008/0077119 | A1 | 3/2008 | Snyder et al. | JP | 10-118193 | 5/1998 |
| 2008/0097247 | A1 | 4/2008 | Eskuri et al. | JP | 10-328191 | 12/1998 |
| 2008/0147170 | A1 | 6/2008 | Vrba | JP | 11-267224 A | 10/1999 |
| | | | | JP | 2000-197704 A | 7/2000 |

FOREIGN PATENT DOCUMENTS

| | | | | | |
|---|---|---|---|---|---|
| BR | PI 9712829 | 1/2000 | JP | 2000-510722 A | 8/2000 |
| CA | 2266685 | 5/2006 | JP | 2000-511083 A | 8/2000 |
| CA | 2255781 | 3/2007 | JP | 3081831 | 8/2000 |
| CN | 1230914 | 10/1999 | JP | 2001-500808 A | 1/2001 |
| DE | 2539191 | 3/1976 | JP | 2002-529137 A | 9/2002 |
| DE | 285514 | 12/1990 | JP | 3325828 | 9/2002 |
| EP | 0 045 931 | 2/1982 | JP | 2002-542901 A | 12/2002 |
| EP | 0 069 522 | 1/1983 | JP | 2002-543896 A | 12/2002 |
| EP | 0 087 933 | 9/1983 | JP | 2003-517893 A | 6/2003 |
| EP | 0 111 044 | 6/1984 | JP | 3649604 | 5/2005 |
| EP | 0 181 174 | 5/1986 | JP | 2005-534407 | 11/2005 |
| EP | 0 377 453 | 7/1990 | SU | 712908 | 1/1980 |
| EP | 0 498 476 | 8/1992 | SU | 758421 | 8/1980 |
| EP | 0 608 853 | 8/1994 | SU | 1529365 | 12/1989 |
| EP | 0 565 065 | 6/1996 | WO | WO 90/02520 | 3/1990 |
| EP | 0 732 117 | 9/1996 | WO | WO 91/13364 | 9/1991 |
| EP | 0 747 089 | 12/1996 | WO | WO 92/04072 | 3/1992 |
| EP | 0 778 038 | 6/1997 | WO | WO 92/07619 | 5/1992 |
| EP | 0 778 039 | 6/1997 | WO | WO 93/04722 | 3/1993 |
| EP | 0 778 040 | 6/1997 | WO | WO 93/11313 | 6/1993 |
| EP | 0 790 066 | 8/1997 | WO | WO 94/06500 | 3/1994 |
| EP | 0 812 599 | 12/1997 | WO | WO 95/01123 | 1/1995 |
| EP | 0 815 894 | 1/1998 | WO | WO 95/24236 | 9/1995 |
| EP | 0 865 772 | 9/1998 | WO | WO 96/19255 | 6/1996 |
| EP | 0 865 773 | 9/1998 | WO | WO 96/33763 | 10/1996 |
| EP | 0 521 595 | 5/1999 | WO | WO 97/10022 | 3/1997 |
| EP | 0 917 885 | 5/1999 | WO | WO 97/25914 | 7/1997 |
| EP | 0 935 947 | 8/1999 | WO | WO 97/37713 | 10/1997 |
| EP | 0 937 481 | 8/1999 | WO | WO 9737713 A1 * | 10/1997 |
| EP | 1 586 274 | 10/2005 | WO | WO 97/43949 | 11/1997 |
| EP | 0 934 141 | 11/2005 | WO | WO 97/44083 | 11/1997 |
| GB | 2214354 | 8/1989 | WO | WO 97/44086 | 11/1997 |
| GB | 2257269 | 1/1993 | WO | WO 98/10694 | 3/1998 |
| JP | 60-091858 | 5/1985 | WO | WO 98/56448 | 12/1998 |
| JP | 61-022752 | 1/1986 | WO | WO 99/04847 | 2/1999 |
| JP | 62-023361 | 1/1987 | WO | WO 99/11313 | 3/1999 |
| JP | 62-089470 | 4/1987 | WO | WO 00/27303 | 5/2000 |
| JP | 62-299277 | 12/1987 | WO | WO 00/30710 | 6/2000 |
| JP | 63-181774 | 7/1988 | WO | WO 00/43061 | 7/2000 |
| JP | 63-217966 | 9/1988 | WO | WO 00/48645 | 8/2000 |
| JP | 10-89956 | 4/1989 | WO | WO 00/57943 | 10/2000 |
| JP | 1-135363 | 5/1989 | WO | WO 00/66199 | 11/2000 |
| JP | 1-158936 | 6/1989 | WO | WO 00/67845 | 11/2000 |
| JP | 2-107268 | 4/1990 | WO | WO 00/72907 | 12/2000 |
| JP | 03-122850 | 12/1991 | WO | WO 01/10492 | 2/2001 |
| JP | 4-061840 | 2/1992 | WO | WO 01/28620 | 4/2001 |
| JP | 4-099963 | 3/1992 | WO | WO 01/36034 | 5/2001 |
| JP | 4-213069 | 8/1992 | WO | WO 01/45773 | 6/2001 |
| | | | WO | WO 01/45912 | 6/2001 |

| | | | | | | |
|---|---|---|---|---|---|---|
| WO | WO 01/93920 | 12/2001 | | WO | WO 2004/047899 | 6/2004 |
| WO | WO 02/062540 | 8/2002 | | WO | WO 2004/110519 | 12/2004 |
| WO | WO 03/004086 | 1/2003 | | WO | WO 2008/030959 | 3/2008 |
| WO | WO 03/008148 | 1/2003 | | | | |
| WO | WO 2004/012804 | 2/2004 | | \* cited by examiner | | |

FIG. 6B under the US 8,377,035 B2

UNBALANCED REINFORCEMENT MEMBERS FOR MEDICAL DEVICE

FIELD OF THE INVENTION

The invention relates generally to medical devices. More specifically, the invention relates to reinforcing members for use in elongate medical devices using braided or helical reinforcing members for support.

BACKGROUND

A variety of elongate thin medical devices such as catheters, endoscopes and the like have been developed over the past several decades. Many of these devices include reinforcement members such as braided, longitudinal or helical elements disposed between an inner layer and an outer layer. During use, it is often necessary for the elongate member to be resistant to kinking while still being flexible and capable of transferring a twisting force. The reinforcement member provides torsional rigidity, column strength, kink resistance, and allows for improved torque response of such elongate members. Where a braid layer is disposed between an inner layer and an outer layer, the braid layer may reduce the structural integrity of the elongate device by limiting the area of adhesion between the inner and outer layers. Further, different aspects of different reinforcement layers, such as filament thickness and number, provide different properties to braids. It is desirable to identify ways to combine positive aspects of several different braid configurations.

SUMMARY

Several embodiments provide a medical device comprising an elongate shaft including a reinforcement member or layer. The reinforcement member or layer may include a plurality of strands, in some embodiments having more strands wound in one direction than in the opposite direction. The strands being designed to preserve the torque and anti-kink properties of the reinforcement layer. In several embodiments the strands in opposing directions are interwoven to construct an unbalanced braid.

In some embodiments, the reinforcement layer or member is disposed between an inner layer and an outer layer. The unique patterns of several such embodiments allow increased contact surface area between the inner layer and the outer layer, without compromising the function of the braid reinforcement layer. Increased contact surface area may enhance the adhesion between the inner layer and the outer layer and improve the structural integrity of the medical device. In turn, improved structural integrity may provide improved performance in terms of torque response, kink resistance and curve performance.

In other embodiments, a reinforcement layer is provided having interwoven strands of different sizes and/or shapes. For example, in one embodiment a braid reinforcement member is provided having a lesser number of larger strands wound in one direction, with a greater number of smaller strands wound in the other direction. By varying sizes, shapes and numbers of strands in a braid layer, torque and anti-kink characteristics of different strand sizes may be combined while reducing braid layer thickness.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

As used herein, the term "about" applies to all numeric values, whether or not explicitly indicated. The term "about" generally refers to a range of numbers that one of skill in the art would consider equivalent to the recited values (i.e. having the same function or result). In many instances the term "about" may include numbers that are rounded to the nearest significant figure.

The invention generally relates to reinforcing structures for use in elongated medical devices. In at least some embodiments, different numbers, shapes, and/or sizes of strands are used to construct unbalanced reinforcing structures.

Figure 1:
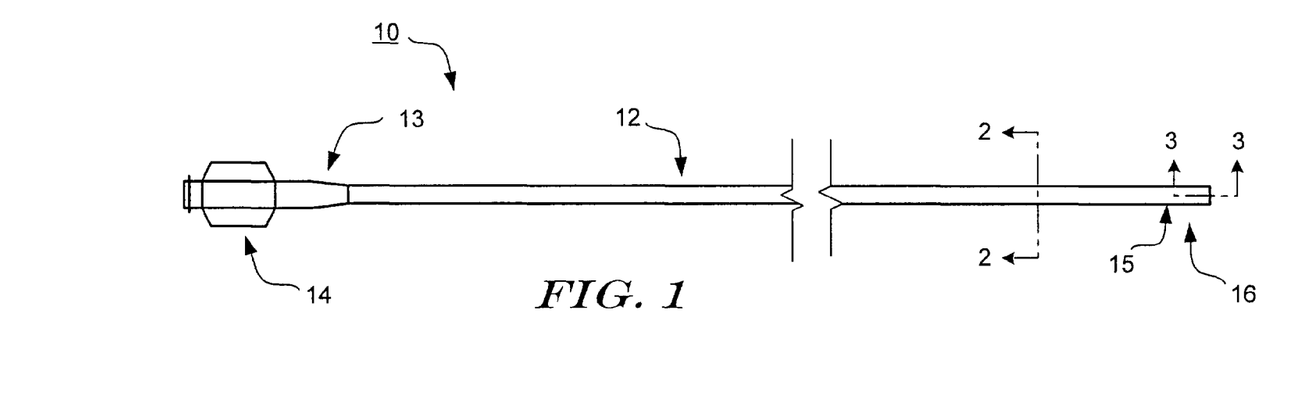
FIG. 1 is a plan view of a medical device in accordance with one example embodiment of the invention, shown as a guide or diagnostic catheter.

Refer now to FIG. 1 which illustrates a medical device 10 in accordance with one example embodiment. In the embodiment shown, the medical device 10 is in the form of a guide or diagnostic catheter. Although set forth with specific reference to a guide or diagnostic catheter, in the example embodiments shown in the Figures and discussed below, the invention may relate to virtually any medical device including an elongate shaft or member having a reinforcing layer disposed therein. For example, the invention may be applied to medical devices such as a balloon catheter, an atherectomy catheter, a drug delivery catheter, a stent delivery catheter, an endoscope, an introducer sheath (if the sheath includes a reinforcing member), a fluid delivery device, other infusion or aspiration devices, device delivery (i.e. implantation) devices, and the like. Thus, while the Figures and descriptions below are directed toward a guide or diagnostic catheter, in other applications sizes in terms of diameter and length may vary widely, depending upon the desired properties of a particular device.

For example, in some devices, lengths may range from about 1-300 centimeters or more, while outside diameters may range from about 1 F to about 20 F, or even more in some embodiments.

The guide or diagnostic catheter 10 may have a length and an outside diameter appropriate for its desired use, for example, to enable intravascular insertion and navigation. For example, the catheter 10 may have a length of about 100 cm-150 cm and an outside diameter of approximately 4 F-9 F, when catheter 10 is adapted as a guide catheter. The guide or diagnostic catheter 10 may include structure and materials that are substantially conventional except as described herein and shown in the drawings. While catheter 10 is described in terms of intravascular use, in other embodiments the guide or diagnostic catheter 10 may be suited for other uses in the digestive system, soft tissues, or any other use including insertion into an organism for medical uses.

The catheter 10 includes an elongate shaft 12 having a proximal end portion 13 and distal end portion 15. A distal tip 16 is connected to the distal portion 15 of the elongate shaft 12. The distal tip 16 and a distal portion 15 of the elongate shaft 12 may be curved as desired depending on the particular application. The elongate shaft 12 and the distal tip 16 include a lumen 18 extending therethrough to facilitate, for example, insertion of other medical devices (e.g., guide wires, balloon catheters, etc.) therethrough, and/or to facilitate injection of fluids (e.g., radiopaque dye, saline, drugs, etc.) therethrough. A manifold 14 is connected to the proximal end of the elongate shaft 12 to facilitate connection to other medical devices (e.g., syringe, Y-adapter, etc.) and to provide access to the lumen 18. In some embodiments, the catheter 10 may exclude the lumen, or may include additional devices such as inflation or anchoring members, sensors, optical elements, ablation devices or the like. In some embodiments, the catheter 10 may be significantly shorter and used as an introducer sheath, for example, while in other embodiments the catheter 10 may be adapted for other medical procedures.

Figure 2:
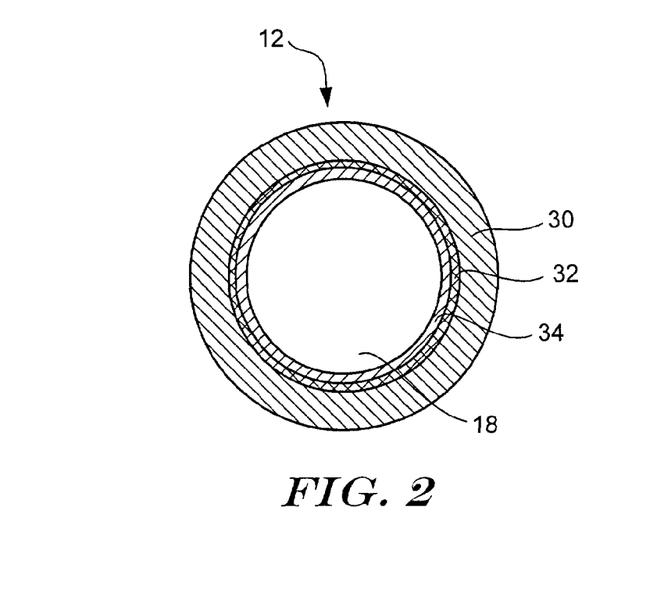
FIG. 2 is a cross-sectional view taken along line 2-2 in FIG. 1.
Figure 3:
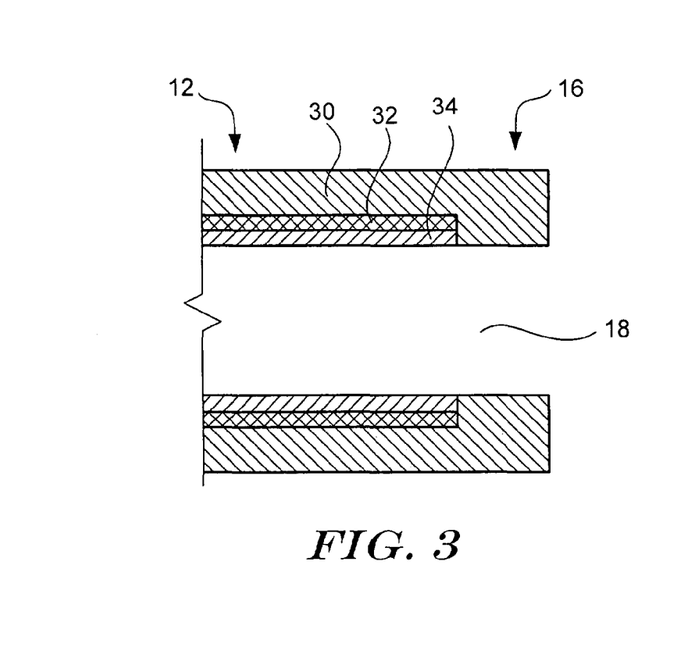
FIG. 3 is a longitudinal sectional view taken along line 3-3 in FIG. 1.

As best seen in FIGS. 2 and 3, the elongate shaft 12 may be multi-layered. In the illustrative embodiment, the elongate shaft 12 may include an outer layer 30, a reinforcement layer 32, an inner layer 34, and a distal tip 16. It should be understood that more or fewer layers can be used depending upon the desired characteristics of the device. Furthermore, while an outer layer 30 and inner layer 34 are described with respect to the particular embodiment, these layers 30, 34 may be provided as a single layer into which a reinforcement layer 32 is later embedded, for example. The inner layer 34 and outer layer 30 may be provided to physically be a single layer with the reinforcement layer 32 providing an "imaginary" dividing line between inner layer 34 and outer layer 30. The distal tip 16 may comprise the outer layer 30 extending beyond the inner layer 34 and the reinforcement layer 32 to define a tip, for example, a soft atraumatic tip. In other embodiments the distal tip 16 may be attached to the rest of catheter 10 in a separate fabrication step.

Inner layer 34 and outer layer 30 may be made of any suitable material and by any suitable process, the materials and processes varying with the particular application. Examples of some suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, etc., or mixtures, blends or combinations thereof, and may also include or be made up of lubricous polymers. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The inner layer 34 may include a lubricious polymer such as HDPE or PTFE, for example, or a copolymer of tetrafluoroethylene with perfluoroalkyl vinyl ether (PFA) (more specifically, perfluoropropyl vinyl ether or perfluoromethyl vinyl ether), or the like. The outer layer 30 may include a flexible polymer such as polyether block amide or polyether-ester elastomer. The outer layer 30 may be formed, for example, by extrusion, co-extrusion, interrupted layer co-extrusion (ILC), or fusing several segments end-to-end. The outer layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In some embodiments, the material of the inner layer 34 and/or outer layer 30 can be blended with a liquid crystal polymer (LCP). For example, the mixture can contain up to about 5% LCP. This has been found to enhance torqueability.

A lubricious, a hydrophilic, a protective, or other type of coating may be applied over portions or all of the shaft 12. Hydrophobic coatings such as fluoropolymers provide a dry lubricity which improves guidewire handling and device exchanges. Lubricious coatings can aid in insertion and steerability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The reinforcement layer 32 may comprise a braid of interwoven strands. The reinforcing member 32 can be of any appropriate size and shape for use in the particular medical device into which it will be incorporated. As shown in FIG. 2, the reinforcing member 32 illustrated has a generally circular cross-sectional shape, and is appropriately sized for use in an intravascular catheter. A broad variety of other shapes and sizes could be used, depending upon the intended use and desired characteristics of the reinforcing member 32. For example, in some embodiments, the reinforcing member 32 could have a flat, curved, oval, or multisided cross-sectional shape, for example, triangular, square, rectangular, pentagonal, hexagonal, and so fourth.

Furthermore, the reinforcing member 32 can be formed using any suitable technique for forming the appropriate reinforcing structure. The braid can be formed using a suitable number of strands or filaments. The number of strands or filaments used in such a braided reinforcing member 32 will often depend upon the desired characteristics of the braid, and the patterns or techniques used to form the braid. In some embodiments, between one and thirty-two, or even more, strands may be used in each direction. Lesser strand numbers are illustrated in the Figures and examples shown herein to facilitate illustration of several embodiments. The strands or filaments should be appropriately sized and shaped depending upon the desired characteristics of the braid and pattern used. In some embodiments, the cross-sectional shape of the filaments can be circular, oval, or multisided, for example, triangular, square, rectangular, pentagonal, hexagonal, and so fourth. In other embodiments, the filaments may be formed as ribbons. The braid density may also vary widely; in some embodiments, the braid density may be as low as about 10 pic; while in other embodiments braid density may increase to the range of about 300 pic.

Reinforcement layer 32 may include strands or fibers of any suitable material. Some examples of suitable materials can include, for example, polymers, metal-polymer composites, metals, metal alloys, or the like, or combinations or mixtures thereof. At least a portion of the reinforcing member 32, or at least some of the filaments or strands making up the reinforcing member 32, can be made of a metallic material, polymeric material, or combinations thereof. In some embodiments or application, suitable metallic materials include, for example, those that can be annealed into a desired shape. Some examples of metallic materials include stainless steel, tungsten, nickel, cobalt, titanium, gold, iridium, or alloys thereof including, for example, nickel-titanium alloy, such as linear elastic or superelastic nitinol, nickel-chromium alloy, nickel-chromium-iron alloy, as well as other such metallic materials, or combinations thereof. Some particular examples of suitable stainless steel alloys include especially high tensile grades, and/or other grades such as 304 and 440A and 440C stainless steel alloys, as well as alloys containing titanium. In some example embodiments, the reinforcing member is a reinforcing braid adapted and configured for use in an intravascular catheter and is formed with primarily stainless steel filaments. For additional embodiments, suitable polymeric materials also include those that can be annealed into a desired shape. Some examples of suitable polymers include nylon, polyesters, acrylics and combinations of mixtures thereof. The strands may also comprise non-metal materials such as liquid crystal polymer (LCP) fibers, glass fibers, etc.

In some embodiments, the reinforcing member 32 includes combinations of filaments or strands made up of different types of materials. For example, in some particular example embodiments, the reinforcing member 32 is a reinforcing braid formed with a combination of stainless steel filaments and tungsten filaments.

The elongate shaft 12 can be constructed using any appropriate technique, for example, by extrusion, a heat bonding process, casting, molding, and the like. For example, in one embodiment braid 32 may be formed over the inner layer 34, which may be supported by a removable mandrel, after which the outer layer 30 may be placed thereon. In some embodiments of the unique braid pattern described herein, the contact surface area between the inner layer 34 and the outer layer 30 is increased relative to conventional designs. This design allows improved connection or adhesion between inner layer 34 and outer layer 30. The enhanced connection between the inner layer 34 and the outer layer 30 may increase structural integrity of the shaft 12 and thereby provide improved performance in terms of torque response and kink resistance and curve performance. For some embodiments, the inner layer 34 and/or outer layer 30 may be excluded.

Figure 4A:
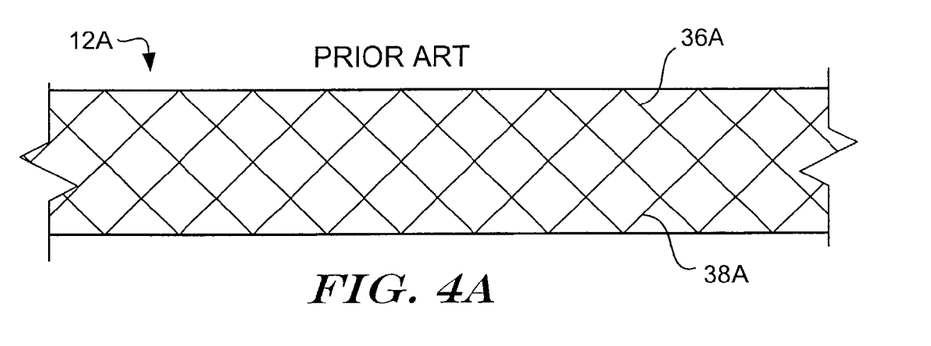
FIG. 4A is a partially sectioned fragmentary view of a prior art catheter shaft schematically illustrating a conventional braid pattern.

As seen in FIG. 4A, a prior art catheter shaft 12A includes a braid reinforcement layer with an equal number of strands 36A/38A wound in each direction at the same pitch. In other words, the same number of strands 36A and strands 38A are wound in opposite directions at the same pitch.

Figure 4B:
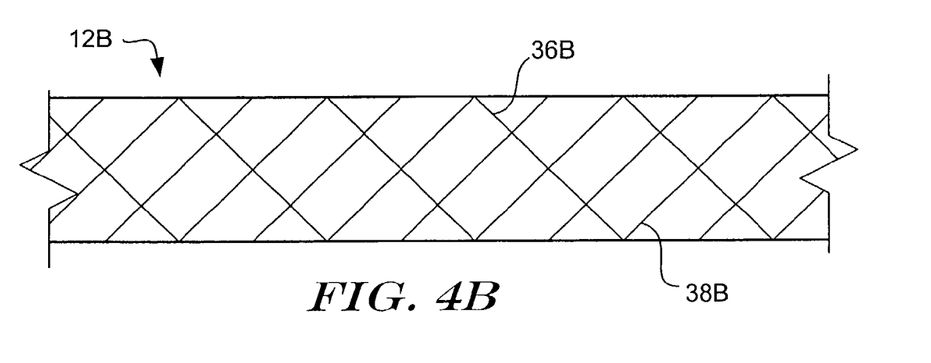
FIG. 4B is a partially sectioned fragmentary view of a medical device shaft in accordance with one example embodiment of the invention, schematically illustrating an unbalanced braid pattern with differing numbers of strands wound in each direction.

By contrast, as seen in FIG. 4B, a catheter shaft 12B in accordance with an example embodiment of the invention may include a braid reinforcement layer with an unequal number of strands 36/38 wound in each direction. The strands 36/38 may be wound at the same pitch as shown in FIG. 4B or at differing pitch as seen in FIG. 4C.

Figure 4C:
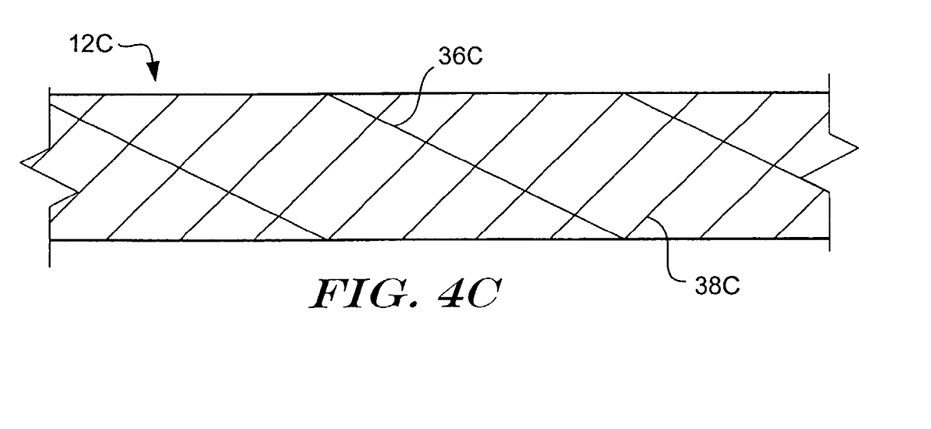
FIG. 4C is a partially sectioned fragmentary view of a medical device shaft in accordance with one example embodiment of the invention, schematically illustrating an unbalanced braid pattern with differing numbers of strands wound in each direction and with differing pitch.

As may be seen from the example embodiments illustrated in FIGS. 4B and 4C, the shaft 12B/12C has increased contact surface area between the inner layer 34 and the outer layer 30, relative to the prior art shaft 12A shown in FIG. 4A. The increased contact surface area enhances the adhesion between the inner layer 34 and the outer layer 30 to thereby improve the structural integrity of the catheter shaft 12B/12C and provide improved performance relative to the prior art shaft 12A.

With continued reference to the embodiment illustrated in FIG. 4B, a first set of one or more strands 36B are wound in a first helical direction and a second set of one or more strands 38B are wound in a second helical direction different than the first helical direction. The number of strands 36B in the first set is different than the number of strands 38B in the second set. Each set wound in each direction may have one or more strands 36B/38B, but differ in number. For example, the number of strands 38B in the second set may be twice the number of strands 36B in the first set, or visa-versa. In one specific example, the first set has 8 strands 36B and the second set has 16 strands 38B, or visa-versa. The braid structures can be, for example, single (eg. one over one), or single-double mixed (e.g. one over two), or double.

As seen in FIG. 4B, the first set of strands 36B may be wound at a first pitch and the second set of strands 38B may be wound at a second pitch, wherein the first pitch is the same as the second pitch. Alternatively, as seen in FIG. 4C, the first set of strands 36C may be wound at a first pitch and the second set of strands 38C may be wound at a second pitch, wherein the first pitch is different than the second pitch.

Figure 5A:
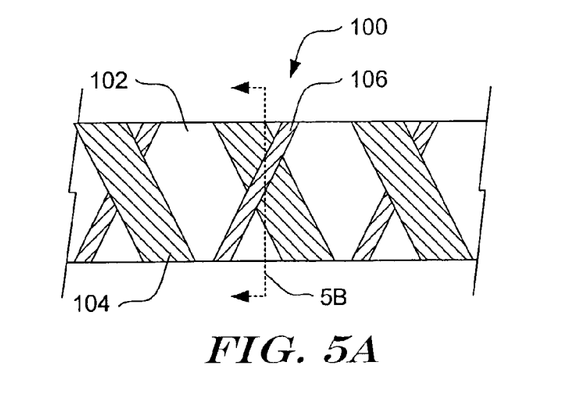
FIG. 5A is a partial side view of an illustrative medical device shaft including an unbalanced braid pattern using different strand sizes on an inner tubular member.
Figure 5B:
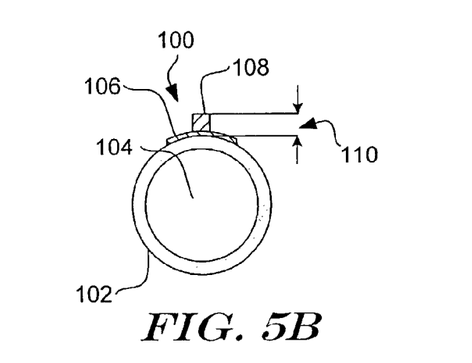
FIG. 5B is a cross sectional view taken along line 5B-5B in FIG. 5A.
Figure 5C:
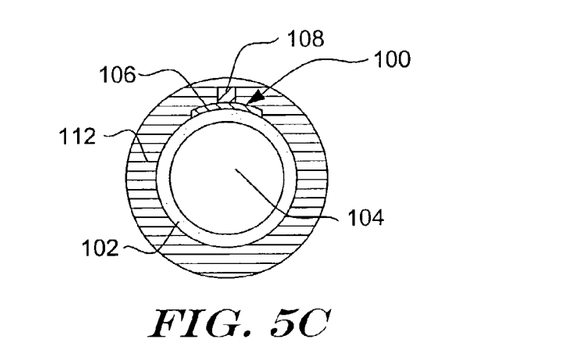
FIG. 5C is a cross sectional view corresponding to FIG. 5B after an additional process step adding an outer layer is complete.
Figure 6A:
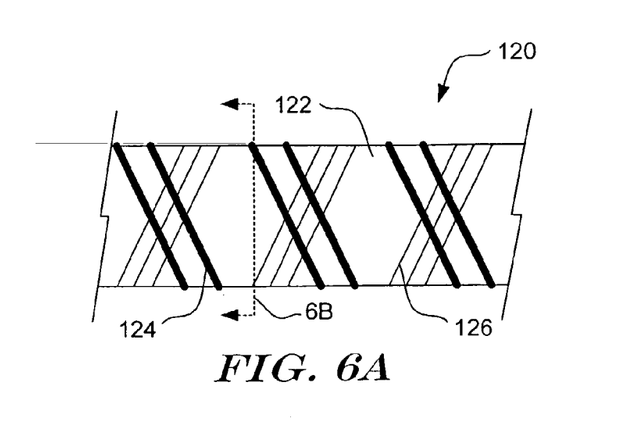
FIG. 6A is a partial side view of an illustrative catheter shaft including another unbalanced braid pattern using a two over three braiding pattern.
Figure 6B:
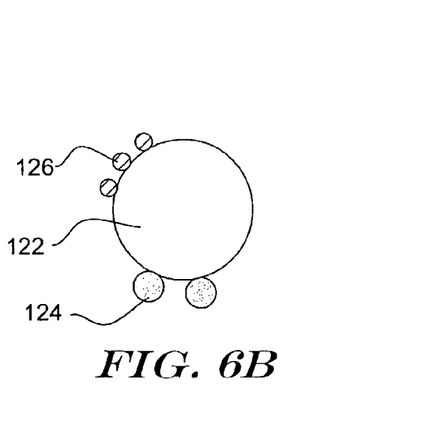
FIG. 6B is a cross sectional view taken along line 6B-6B of FIG. 6A.

While the example embodiment shown in FIGS. 4B and 4C is "unbalanced" in that the number of strands wound in one direction is different from the number of strands wound in the opposed direction, the unbalanced braiding in FIGS. 5A-5C uses strands of different shapes and weights. In other embodiments, a braid structure having strands of different shapes (cylindrical wires versus ribbons, for example), using strands of different compositions (multi-filament versus single filament, strands of different materials, etc.), uneven weaving patterns (for example a three-over-two pattern as shown in FIG. 6), or combinations thereof, are included.

FIGS. 5A-5C illustrate another example embodiment of a medical device in which the strands chosen are of different sizes. In FIG. 5A, a braid 100 is placed over a tubular member 102 having a lumen 104. The braid 10Q includes wide, thin strand 106 wound in a first direction and narrow, thick strand 108 wound in the opposing direction. The wide thin strand 106 provides strong torque response in the first direction. The narrow, thick strand 108 provides strong kink resistance and torque response in the opposing direction. The combined braid 100 therefore has strong torque response in both directions as well as strong kink resistance.

FIG. 5B illustrates a cross sectional view of the example embodiment in FIG. 5A. In particular, the crossing over of thin strand 106 and thick strand 108 is highlighted. Notably, the height 110 of the crossing is less than it would be if there were two thick strands 108 crossing at the same location. Because the height of the braid crossing is reduced while maintaining strong anti-kink and torque response characteristics, the outer layer 112 shown in FIG. 5C may be thinner. Likewise, by reducing the crossing thickness of the braid 100, the likelihood of ripples or wrinkles in the outer layer 112 or pushing through the inner layer 102 may be reduced. Such wrinkles or ripples can introduce friction and/or points of weakness to the inner and outer layers of a medical device, and can make introduction of a medical device into the vasculature of a patient more traumatic and difficult, while also potentially impeding the progress of materials or devices advanced or withdrawn through the inner lumen 104.

In the illustrative embodiment shown, the relative thicknesses and widths of the ribbons may vary widely, noting of course that the drawings are not necessarily to scale. For example, a braid may have a wide, thin ribbon 104 that is one mil thick and five mils wide wound in one direction, with narrower, thicker ribbon 106 being two mils thick and three mils wide, wound in the opposing direction. The height of a braid crossing for such a combination is three mils, yet the kink resistance (which is generally a function of ribbon, filament or strand thickness) is higher or better than the kink resistance of two ribbons of equal thickness at one and one half mils. While the kink resistance is improved, the torque response is maintained by making the thinner ribbon 104 wider, to maintain high torque response in the one direction; torque response in the other direction can be maintained as well by using the thicker ribbon 106.

Braid thicknesses ranging from as little as about one quarter of one mil up to ten mils can be incorporated into various embodiments, and both larger and smaller thicknesses may be used as well. Some embodiments uses braid thickness in the range of about 0.2 mils to about 6 mils. Other embodiments allow braid thickness in the range of about 1 mil to about 3 mils. Further, braid widths may also vary widely, without deviating from the spirit and scope of the present invention. Some embodiments use braid widths in the range of about 0.25 mils to about 7 mils. Other embodiments include braid widths in the range of about 3 mils to about 5 mils.

FIG. 6 illustrates another embodiment of an unbalanced braid 120. Unbalanced braid 120 has been wound upon mandrel 122. After the braid 120 is complete, it may be relaxed or otherwise released from the mandrel and placed over a lubricious inner layer of a medical device, for example, or otherwise embedded or integrated into a medical device using a braided support structure.

Braid 120 includes relatively thick strands 124 and relatively thin strands 126. Notably, less of the thick strands 124 are included in the braiding than the thin strands 126. Such a combination may again provide a braid structure combining the strong torque characteristics of thin strands 126 with the strong anti-kink and torque characteristics of thick strands 124.

Braid 120 includes the thick strands 124 in a two-over three braiding with respect to the thin strands 126. Such a combination allows a braid 120 to be designed with particular torque response desired without sacrificing kink resistance while keeping braid wall thickness (i.e. the crossing thickness 112 shown in FIG. 5B) the same.

For example, given a 1.0 mil single strand with 2.0 mil single strand braid crossed at, for example, 140 pic, sufficient anti-kink response may be provided largely by the 2.0 mil single strand, but the torque on the 1.0 mil single strand direction may be insufficient for a given application. The braid crossing would be at 3.0 mils. To keep the braid crossing at 3.0 mils, a 1.25 mil single strand with 1.75 mil single strand braid at 140 pic could be tried. However, going from the 2.0 mil single strand to the 1.75 mil single strand would reduce anti-kink response significantly, such that the new structure may show sufficient torque but fail with respect to kink response.

A different approach, as suggested herein, is to provide a 1.0 mil double strand with 2.0 mil single strand at 140 pic. The new configuration would provide greater torque than a single/single design, but without sacrificing braid wall thickness (crossings remain at 3.0 mils) or anti-kink response provided by the 2.0 mil single strand. In this illustrative approach, the braid may include a first winding and a second winding, where the second winding provides a much greater portion of the anti-kink resistance of the braid, while both windings contribute similarly to the torque response of the winding.

The materials used in the strands of braid 120 may be combined advantageously as well. For example, tungsten wires may be used for the smaller wires to provide good radiopaque qualities with strong torque response and manufacturability, while the thicker wires could be chosen to be made of high tensile strength stainless steel (HTSS).

Some example combinations of wires and sizes, for example in the embodiment shown in FIG. 6, may include the following:

triple 1 mil tungsten by double 1.5 mils HTSS;
triple 1 mil tungsten by double 1.75 mil HTSS;
triple 1.25 mils tungsten by double 1.75 mil HTSS;
triple 1.25 mils tungsten by double 2 mil HTSS;
quadruple 1 mil HTSS by double including a single 2 mil tungsten and single 2 mil HTSS; and
quadruple 125 mil HTSS by double 1.25 mils tungsten.

Many other example combinations of wires and sizes can also be used, depending upon the desired characteristics, for example torque and anti-kink characteristics. Additionally, the individual wires may be mixed with regard to material of manufacture, for example, the thick wires may include one made of a polymer and one made of HTSS. As shown in several embodiments, a triple one mil or above tungsten with double one and a half mil or above HTSS is suggested to obtain good results in the given illustrative embodiments. In other embodiments a variety of ranges may be desirable for example, making the smaller wires in the range of about 0.25 mils to about 1.5 mils in diameter, while making the larger wires in the range of about 1.25 to about 4 mils in diameter. Another embodiment uses smaller wires in the range of about 0.5 mils to about 1.25 mils in diameter, while using larger wires in the range of about 1.5 mils to about 2 mils diameter.

One of skill in the art will recognize that the materials and ranges may be greatly varied without deviating from the scope of the present invention. Indeed, a double/double combination using different sizes, shapes, or materials between the two windings may prove highly desirable, as may other numeric combinations. For example, ribbon shapes may be used in combination with wires. Likewise, the wires, while shown in the Figures as being generally circular in cross section may instead be oval-shaped, rounded ribbons, triangular, or may include different geometrical cross sections. As used in this document, including the claims, the term round includes a generally circular or oval cross section.

Those skilled in the art will recognize that the present invention may be manifested in a variety of forms other than the specific embodiments described herein. Accordingly, departures in form and detail may be made without departing from the scope and spirit of the present invention as described in the appended claims.

What is claimed is:

1. A medical device comprising:
an elongate shaft including a reinforcement layer, the reinforcement layer comprising a plurality of interwoven strands forming a braid, with a first set of one or more strands wound in a first helical direction and a second set of one or more strands wound in a second helical direction different than the first helical direction, and wherein the number of strands in the first set is less than the number of strands in the second set; wherein the first set of strands is wound at a first pitch and the second set of strands is wound at a second pitch, wherein the first pitch is different than the second pitch.

2. A medical device as in claim 1, wherein the first set has one strand and the second set has a plurality of strands.

3. A medical device as in claim 1, wherein the first set has two strands and the second set has four strands.

4. A medical device as in claim 3, wherein one of the two strands of the first set comprises tungsten and the other of the two strands the first set comprises stainless steel, and the four strands of the second set comprise stainless steel.

5. A medical device as in claim 3, wherein the two strands of the first set comprise tungsten and the four strands of the second set comprise stainless steel.

6. A medical device as in claim 1, wherein the strands within the first set are larger than the strands within the second set.

7. A medical device as in claim 5, wherein the strands in the first set and the second set are ribbons.

8. A medical device as in claim 6 wherein the strands in the first set and the second set have a round cross section.

9. A medical device as in claim 1, wherein the number of strands in the first set is twice the number of strands in the second set.

10. A medical device as in claim 9, wherein the first set has 1 strand and the second set has 2 strands.

11. A medical device as in claim 1, wherein the elongate shaft further includes an inner layer, with the reinforcement layer disposed about the inner layer.

12. A medical device as in claim 1, wherein the elongate shaft further includes an outer layer disposed about the reinforcement layer.

13. A medical device as in claim 1, wherein the elongate shaft further includes an inner layer and an outer layer, with the reinforcement layer disposed between the inner layer and the outer layer.

14. A medical device as in claim 13, wherein the outer layer extends distally beyond the reinforcement layer and the inner layer to define an atraumatic tip.

15. A medical device comprising an elongate shaft including a reinforcement layer comprising a first layer of ribbons wound in a first direction and a second layer of ribbons wound in a direction opposed to the first direction, the ribbons in the first layer being of a different size from the ribbons of the second layer; wherein the first layer of ribbons is wound at a first pitch and the second layer of ribbons is wound at a second pitch different from the first pitch.

16. The medical device of claim 15 wherein the ribbons of the first layer are wider than the ribbons of the second layer.

17. The medical device of claim 15 wherein the ribbons of the second layer are thicker than the ribbons of the first layer.

18. The medical device of claim 15 wherein the ribbons of the second layer are adapted to provide greater kink resistance than the ribbons of the first layer.

19. The medical device of claim 18 wherein the ribbons of the first layer are wider and thinner than the ribbons of the second layer.

20. A braided reinforcement member for use in a medical device, the braided reinforcement member comprising:
    a first set of one or more strands wound in a first helical direction; and
    a second set of one or more strands wound in a second helical direction different from the first helical direction;
    wherein the number of strands in the first set is different from the number of strands in the second set;
    wherein the first set of strands is wound at a first pitch and the second set of strands is wound at a second pitch, wherein the first pitch is different than the second pitch.

21. A method of forming a braided reinforcement member for use in a medical device, the method comprising:
    winding a first set of one or more strands in a first helical direction; and
    winding a second set of one or more strands in a second helical direction;
    wherein the winding of the first set and the winding of the second set is performed to result in a braided element including the first set and the second set; wherein the first set of strands is wound at a first pitch and the second set of strands is wound at a second pitch, wherein the first pitch is different than the second pitch; and wherein the number of strands in the first set is different from the number of strands in the second set.

22. A braided reinforcement member for use in a medical device, the braided reinforcement member comprising:
    a first set of one or more strands wound in a first helical direction; and
    a second set of one or more strands wound in a second helical direction different from the first helical direction;
    wherein the size of at least one strand in the first set is different from the size of at least one strand in the second set; wherein the number of strands in the first set is different from the number of strands in the second set; and wherein the first set of strands is wound at a first pitch and the second set of strands is wound at a second pitch, the second pitch different than the first pitch.

23. A method of forming a braided reinforcement member for use in a medical device, the method comprising:
    winding a first set of one or more strands in a first helical direction; and
    winding a second set of one or more strands in a second helical direction;
    wherein the winding of the first set and the winding of the second set is performed to result in a braided element including the first set and the second set; and wherein the size of at least one strand in the first set is different from the size of at least one strand in the second set; wherein the number of strands in the first set is different from the number of strands in the second set; and wherein the first set of strands is wound at a first pitch and the second set of strands is would at a second pitch, the second pitch different than the first pitch.

* * * * *